(12) United States Patent
Levin

(10) Patent No.: US 7,731,711 B2
(45) Date of Patent: *Jun. 8, 2010

(54) CRYOSURGICAL INSTRUMENT AND ITS ACCESSORY SYSTEM

(75) Inventor: Alexander Levin, Binyamina (IL)

(73) Assignee: Arbel Medical Ltd., Caesarea (IL)

( * ) Notice: Subject to any disclaimer, the term of this patent is extended or adjusted under 35 U.S.C. 154(b) by 0 days.

This patent is subject to a terminal disclaimer.

(21) Appl. No.: 12/336,866

(22) Filed: Dec. 17, 2008

(65) Prior Publication Data

US 2009/0125008 A1 May 14, 2009

Related U.S. Application Data

(63) Continuation of application No. 11/531,058, filed on Sep. 12, 2006, now Pat. No. 7,481,806, which is a continuation of application No. 10/637,904, filed on Aug. 11, 2003, now Pat. No. 7,137,978.

(30) Foreign Application Priority Data

Aug. 26, 2002 (IL) ...................................... 151486

(51) Int. Cl.
*A61B 18/18* (2006.01)

(52) U.S. Cl. .......................................... 606/22; 606/23
(58) Field of Classification Search .............. 606/20–26
See application file for complete search history.

(56) References Cited

U.S. PATENT DOCUMENTS

| 3,971,383 | A | 7/1976 | van Gerven |
| 5,254,116 | A | 10/1993 | Baust |
| 5,324,286 | A | 6/1994 | Fowle |
| 5,573,532 | A | 11/1996 | Chang |
| 5,674,218 | A | 10/1997 | Rubinsky |
| 5,716,353 | A | 2/1998 | Matsuura |
| 5,814,040 | A | 9/1998 | Nelson et al. |
| 6,059,820 | A | 5/2000 | Baronov |
| 6,200,308 | B1 | 3/2001 | Pope et al. |
| 6,251,105 | B1 * | 6/2001 | Mikus et al. ................... 606/22 |
| 6,383,180 | B1 * | 5/2002 | Lalonde et al. ............... 606/22 |
| 6,432,102 | B2 * | 8/2002 | Joye et al. ..................... 606/21 |
| 6,682,525 | B2 | 1/2004 | Lalonde et al. |
| 2003/0220635 | A1 | 11/2003 | Knowlton et al. |

* cited by examiner

*Primary Examiner*—Michael Peffley
(74) *Attorney, Agent, or Firm*—Heslin Rothenberg Farley & Mesiti P.C.

(57) ABSTRACT

The invention proposes a cryosurgical instrument and its accessory system operating on the base of a refrigerant evaporation. The invention comprises combination of some technical solutions. Flow in a central lumen of the cryosurgical instrument has oscillating character; the refrigerant is provided on the internal surface of the distal cryotip in the form of separated portions. 2. The internal surface of the distal cryotip of the cryosurgical instrument is covered by a porous coating, which soaks completely one portion of the refrigerant. 3. Vapors obtained as a result of the refrigerant boiling on the porous coating of the cryotip are removed through the central lumen into the atmosphere. Combination of these technical solutions allows to construct a safely cryosurgical instrument with high freezing power and small outer diameter. The proposed cryosurgical instrument may be designed as a flexible cryocatheter or as a rigid cryoprobe.

12 Claims, 7 Drawing Sheets

CRYOSURGICAL INSTRUMENT AND ITS ACCESSORY SYSTEM

CROSS REFERENCE APPLICATION

This patent application is a continuation application of non-provisional application Ser. No. 11/531,058 filed 12 Sep. 2006, now U.S. Pat. No. 7,481,806, which is a continuation of non-provisional application Ser. No. 10/637,904 filed 11 Aug. 2003, now U.S. Pat. No. 7,137,978, which claims the benefit of the earlier filed Israeli Patent Application Ser. No. 151486 filed 26 Aug. 2002, all of which applications are hereby incorporated herein by reference in their entirety.

FEDERALLY SPONSORED RESEARCH OR DEVELOPMENT

Not Applicable.

BACKGROUND OF THE INVENTION

There is significant number of patents, especially, the USA patents, which describe different constructions of cryosurgical probes and catheters. An aim of these patents is to solve some main problems, which are common to cryosurgical probes and catheters.

The problems include construction of relatively cheap and simple probes or catheters with high reliability and sufficiently effective thermal insulation of their lateral non-operating walls. Besides, cryosurgical catheters must have high flexibility, especially, when they are used for cardiac interventions. At the same time the closed distal end (cryotip) of such probe or catheter must provide in many cases high specific freezing capacity at sufficiently low-temperatures.

Analysis of USA patents related to this field shows, that constructions of the proposed probes and catheters intended for cryosurgery do not conform the above-mentioned requirements.

For example, U.S. Pat. No. 3,971,383 proposes a cryogenic surgical instrument with a coaxial assembly of the flexible lumens; the inner one being connected to a supply of cryogenic liquid, and the space between the outer wall of the inner lumen and the next lumen forming a return line for evaporated cryogenic liquid which is vented to the atmosphere; and the space between the outermost one of the coaxial lumens and the intermediate lumen containing a gas, such as normal butane, serving for thermal insulation of the inner and intermediate lumens.

U.S. Pat. No. 5,716,353 describes a probe for cryosurgery which consists of three lumens: an inner lumen for supply a cryogenic refrigerant to a cryotip positioned on the distal end of an outer jacket lumen, and an intermediate lumen situated concentrically around the inner lumen. The channel between the inner and intermediate lumens serves as a venting path for venting cryogenic refrigerant from the freezing zone. This construction is simple, but it does not provide sufficient thermal insulation as required in construction of a cryogenic catheter. Consequently, it may cause over-heating of the venting cryogenic refrigerant, as well as over-cooling of tissues adjacent the intermediate section of the catheter.

U.S. Pat. No. 5,573,532 describes design of a cryosurgical instrument, which comprises lumens of cryogenic fluid supply and return of cryogenic fluid vapors; these lumens are situated concentrically and the return lumen is sealed with a cryotip. The patent proposes to do vacuum insulation of the return lumen. Such construction is very expensive and has low reliability. Besides, this vacuum insulation limits flexibility of the probe, especially, when it has significant length and is used as a catheter.

U.S. Pat. No. 5,674,218 describes a cryosurgical instrument, a system and method of cryosurgery. According to this patent a cryogenic liquid (preferably, liquid nitrogen) is preliminary sub-cooled below its normal boiling point and in such condition it is supplied into the open proximal end of the internal supply line. The outer lumen of the cryosurgical instrument is provided with active vacuum insulation.

Obviously, this construction cannot ensure high flexibility and cannot be used as the base for construction of a catheter for cryosurgery.

U.S. Pat. No. 5,254,116 describes a cryocatheter with a set of vent holes in the lateral wall of a central feeding lumen; besides, sub-cooled liquid nitrogen is delivered into the central feeding lumen as a cryogenic liquid. This construction does not ensure proper thermal insulation of the cryocatheter.

BRIEF SUMMARY OF THE INVENTION

This invention proposes novel designs of a cryosurgical instrument and its accessory system. The cryosurgical instrument is constructed from two major sub-units: a distal cryotip, which serves for immediate contact with a target tissue to be treated; freezing action of this cryotip is obtained by evaporation of a cryogenic liquid on its internal surface covered with a porous coating with open porosity; an elongated tubular sub-unit serving for delivery of portions of the cryogenic liquid on the distal cryotip with following removal of vapors generated in the process of boiling this cryogenic liquid in the porous coating of the distal cryotip.

The elongated tubular sub-unit in turn comprises following details: an external shaft and a central feeding-venting lumen, which serves for immediate supply of portions of the cryogenic liquid to the porous coating of the distal cryotip and, at the same time, for removal of the vapors, generated in the process of boiling the cryogenic liquid on the internal surface of the distal cryotip, into the atmosphere or into a vacuum pump.

In addition, there is a coaxial tubular piece positioned in the gap between the distal sections of the central feeding-venting lumen and the external shaft; the distal end of this coaxial tubular piece is sealed with the external shaft or with the cryotip itself and the proximal end—with the central feeding-venting lumen. It forms a buffer space between: the internal surface of the cryotip, the central feeding-venting lumen and the coaxial tubular piece, this buffer space facilitates flow of the portion the cryogenic liquid in the central feeding-venting lumen toward the cryotip.

The proximal section of the external shaft and proximal end of the central feeding-venting lumen are provided with inlet-outlet connections.

In another version there is a coaxial intermediate lumen, which is situated between the central feeding-venting lumen and the external shaft. This coaxial intermediate lumen substitutes the aforementioned coaxial tubular piece. The distal end of this coaxial intermediate lumen is sealed with the external shaft or with the cryotip itself; the proximal end—with the central feeding-venting lumen, and the proximal end of the external shaft—with the proximal section of the coaxial intermediate lumen. The proximal section of the coaxial intermediate lumen is provided in this case with an outlet connection.

When the proposed construction is used as a cryocatheter, the external shaft is made preferably from polymer material, it allows to achieve its high flexibility.

The cryotip of the cryocatheter should be made from material with high thermal conductivity (for example, copper, silver, diamond, BeO). As it has been noted, the internal surface of cryotip is covered with a porous coating with open porosity (for example, this porous coating is obtained by sintering copper powder). This provides high magnitudes of the heat transfer coefficients in the process of boiling the cryogenic liquid. Besides, this porous coating can completely soak one portion of the cryogenic liquid provided by an accessory system during first quarter-period of its operation as it will be described thereafter.

The proposed cryocatheter can be used for inhibiting restenosis of a blood vessel. In this case the cryotip is constructed in the form of a tubular detail, the distal end of the tubular detail is sealed with a plug from polymer with low thermal conductivity and its tubular section is fabricated from a thin polymer film with high elasticity, the internal surface of the tubular section is coated with a porous polymer layer with open porosity, this porous polymer layer has also high elasticity.

Construction of the accessory systems for these two designs of the cryocatheter (or cryoprobe) will be described thereafter as well.

A first version of the accessory system, which ensures desired functioning of the proposed cryosurgical instrument, comprises: a thermo-insulated tank filled with the cryogenic liquid, the thermo-insulated tank is provided with a relief valve which gives possibility to preset the desired pressure in this thermo-insulated tank; a feed pipe which is situated vertically and the lower end of this feed pipe is positioned near the bottom of the thermo-insulated tank. An outlet connection of the feed pipe is joined by a flexible thermo-insulated duct with an inlet connection of a multi-way valve. This multi-way valve is provided with an additional inlet connection which is communicated with a bottle with pressurized gas (for example, nitrogen), an outlet connection which is communicated with atmosphere (or a vacuum pump), and with an inlet-outlet connection which is communicated with an inlet-outlet connection of the central feeding-venting lumen of the cryosurgical instrument itself.

In addition, there are four shut-off valves, the first shut-off valve is installed on a main duct which communicates the multi-way valve with the inlet-outlet connection of the central feeding-venting lumen of the cryosurgical instrument, the second one—on a duct which communicates the outlet connection of the thermo-insulated tank with the multi-way valve, the third one—on the duct which communicates the bottle with pressurized gas and the multi-way valve, and the fourth—on the thermo-insulated tank itself; this shut-off valve serves for filling the thermo-insulted tank with the cryogenic liquid. The fourth shut-off valve is open during filling the thermo-insulated tank with the cryogenic liquid; the second one serves for cutting off supply of the cryogenic liquid to the multi-way valve, the third one—for cutting off supply of pressurized gas to the multi-way valve and the first one—for putting in action the cryosurgical instrument.

An electromechanical (or pneumatic) drive ensures periodical with preset frequency changeover of the multi-way valve in such a way, that it is communicating alternatively with: the thermo-insulated tank, the bottle with pressurized gas, and the atmosphere (or the vacuum pump).

A control unit keeps watch on frequency of changeover of the multi-way valve and, in the case of significant deviation from the preset frequency of changeover or its stoppage, this control unit activates the aforementioned second and third shut-off valves. In addition, it is possible to install pressure and temperature gauges on the main duct of the accessory system. Data provided from these gauges-are processed in the control unit. In the case of significant deviations of the measured parameters from the preset values, the control unit cuts off the shut-off valves installed on the main, first and second ducts.

Significant fraction of the cryogenic liquid, which remains in the porous coating of the cryotip and in the aforementioned buffer space in the period between communication of the central feeding-venting lumen with the inlet connection of the vacuum pump (or with the atmosphere) and communication this central feeding-venting lumen with the feeding pipe of the thermo-insulated tank, generates reasonably high pressure in the central feeding-venting lumen; this pressure prevents introducing the following portion of the cryogenic liquid into the central feeding-venting lumen.

In the aforementioned case of application of the coaxial intermediate lumen with an outlet connection instead of the coaxial tubular piece, there is an auxiliary shut-off valve installed on a duct communicating the outlet connection of the coaxial intermediate lumen with the atmosphere (or with the vacuum pump); this shut-off valve is joined with the multi-way valve mechanically or electro-mechanically in such a way, that it will be open only at a quarter-period, when the multi-way valve is communicating the main duct with the bottle with pressurized gas.

In addition, the outlet connection of the intermediate lumen can serve as an inlet-outlet connection. In this case a gas from a special bottle is provided into the gap between the coaxial intermediate and the central feeding-venting lumens; introduction of this gas is performed when the multi-way valve communicates the central feeding-venting lumen with the atmosphere (or the vacuum pump).

The ducts between the thermo-insulated tank and the multi-way valve, and between this multi-way valve and the inlet-outlet connection of the central feeding-venting lumen can be provided with outer thermal insulation, for example, with vacuum insulation.

There are several cryogens that can be applied as the cryogenic liquid: liquid nitrogen, liquid argon, liquid R14 and others.

Besides, it is possible to apply two tanks with different liquids: the first one—a cryogenic liquid with low temperature of boiling (for example, liquid nitrogen), which serves for cryogenic treatment of target tissue, and the second one—with relatively high temperature of boiling (for example, R12B1 that boils at temperature −3.8.degree. C. at atmospheric pressure), this second liquid serves for ice-mapping.

The second liquid with normal boiling temperature higher than 0.degree. C. (for example, R11, which has normal boiling temperature 23.65.degree. C.) can be used for fast thawing a tissue, which has been previously frozen by the cryogenic liquid.

Application of two liquids with high difference in their boiling temperatures requires performance of blowing the central feeding-venting lumen, the buffer space and several ducts in the period between the procedures of ice-mapping (or thawing) and following cryogenic treatment.

The accessory system comprises in this case two accessory sub-systems, each of these accessory sub-systems is constructed much as the accessory system, which has been described above. The accessory sub-systems have a common control unit and a common main duct which splits off into two ducts communicated correspondingly with first and second multi-way valves; a thermo-insulated tank of the first accessory sub-system contains a cryogenic liquid which serves to freeze the target tissue, and a tank of the second accessory subunit contains a liquid with relatively high temperature of boiling (for example, R12B1 or R11), this liquid serves for preliminary ice-mapping (as with R12B1); or for fast thawing this target tissue (as with R11).

The accessory system comprises in addition an auxiliary accessory sub-system, which serves for blowing the cryosurgical instrument and the ducts communicating the first and second accessory sub-systems with this cryosurgical instrument. The auxiliary accessory sub-system consists of an auxiliary bottle with pressurized gas and an auxiliary three-way valve, which is installed on a duct communicating the auxiliary bottle with the main duct. The auxiliary three-way valve is regulated by the common control unit, and it has two outlet connections, the first outlet connection of this auxiliary three-way valve is communicated with the main duct and the second one—with the atmosphere or a vacuum pump.

Blowing process is performed by cutting out the shut-off valves installed on the ducts communicating the tanks with their associated multi-way valves and then pressurized gas from the bottle performs blowing the main duct and the ducts generated by its splitting off, the central feeding-venting lumen and the buffer space by charging and purging technique.

As stated above, the gap between the central feeding-venting lumen (or the coaxial tubular piece) and the external shaft serves for thermal insulating the external shaft, especially, its distal section in order to prevent possibility of negative temperature on its outer surface.

It is possible to achieve higher degree of thermal insulation of the external shaft of the cryosurgical instrument by preliminary filling the gap between the external shaft and the coaxial tubular piece with a gas, which has very low thermal conductivity, and, on the other hand, condensation temperature of this gas is lower than the boiling temperature of the cryogenic liquid. In order to perform this filling, the proximal section of the external shaft is provided with an inlet-outlet connection; the accessory system comprises a bottle with the aforementioned gas with low thermal conductivity, and a duct, which communicates this bottle with the inlet-outlet connection of the external shaft, is provided with a three-way valve, which is communicated as well with the atmosphere or with a vacuum pump. It allows to perform filling the gap between the external shaft and the coaxial tubular piece by charging and purging technique.

In order to achieve better characteristics of thermal insulation of the distal section of the external shaft (to prevent negative temperature of its outer surface) it is possible to apply a heat pipe principle.

In this case, the heat pipe principle is realized in the following manner: the outer surfaces of the coaxial tubular piece and a section of the central feeding-venting lumen mating this coaxial tubular piece are covered with a porous coating with open porosity, this coating is functioning as a wick. The gap between the external shaft and the coaxial tubular piece, and its extension to the gap between the central feeding-venting lumen and the external shaft is filled with such a gas that the temperature of its condensation somewhat higher than the boiling temperature of the cryogenic liquid, but the solidification temperature of this gas should be somewhat lower than the boiling temperature of the cryogenic liquid. This gas can be provided into these gaps via the inlet-outlet connection installed on the proximal section of the external shaft.

Charging and purging technique can perform it. Such technical solution permits to heat the distal section of the external shaft at the expense of the heat provided to the intermediate and proximal sections of the external shaft from the surroundings.

It should be noted that the multi-way valve can be substituted for a set of shut-off valves installed on the communicating ducts; coordinated operation of this set of the shut-off valves simulates operation of the aforementioned multi-way valve.

The cryosurgical instrument constructed according to this invention can be provided with a thermocouple, which is positioned in the cryotip and measures temperature in this cryotip in the process of a cryosurgical operation.

Besides, if the cryosurgical instrument is designed as a cryocatheter, this cryocatheter should be provided with a steering mechanism allowing bending its distal section.

The cryotip of the cryocatheter (or cryoprobe) may be provided with an electrode for preliminary detection of electrical signal activity of different places of the organ to be operated.

Operation of the cryosurgical instrument and its accessory system is performed in a following manner.

A portion of the cryogenic liquid is introduced via the feed pipe of the thermo-insulated tank into the duct communicating the multi-way valve with the inlet-outlet connection installed on the proximal end of the central feeding-venting lumen (in the following, this duct will be called—the main duct), it occurs at a quarter-period, when the multi-way valve is in such position, that the cryogenic liquid may flow from the feed pipe into the main duct (it is a first quarter-period).

Thereafter the multi-way valve ceases flow of the cryogenic liquid from the thermo-insulated tank into the main duct and at the following second quarter-period the multi-way valve communicates the bottle with the pressurized gas with the main duct, which provides high velocity to the portion of the cryogenic liquid and this portion passes briefly the main duct and the central feeding-venting lumen, and reaches the porous coating of the cryotip.

Then supply of the pressurized gas is ceased and the multi-way valve cuts off the proximal end of the main duct. The cryogenic liquid is boiling in the porous coating of the cryotip with elevation of pressure of the cryogenic liquid vapor in the central feeding-venting lumen and the main duct (it is a third quarter-period).

At the fourth quarter-period the multi-way valve turns on the duct communicating the main duct with the atmosphere or with the vacuum pump. Boiling the cryogenic liquid in the porous coating of the cryotip can be continued in this quarter-period. It is well to bear in mind that all aforementioned quarter-periods may have different duration.

In the case when the cryosurgical instrument is designed as a cryocatheter, which is intended to treat a blood vessel in order to prevent restenosis and its cryotip is constructed from elastic polymer, it is very important to keep relatively low excessive pressure in the internal chamber of the distal section of this cryocatheter with small deviation from its average value. In order to provide these conditions, the cryocatheter is constructed with the intermediate lumen as it has been described above. The outlet connection of the intermediate lumen is provided with a T-shaped manifold, which comprises a crossbar and a main section intersecting perpendicularly with the crossbar. A pressure gauge is installed on one end of the crossbar and an adjusting valve is installed on the other end, this adjusting valve is connected with the atmosphere or with the vacuum pump. Signals from the pressure gauge are sent to a pressure control unit, which provides in turn desired operation of the adjusting valve. It should be noted that the pressure control unit could be interconnected with the aforementioned control unit, in doing so operations of these control units are correlated.

It is the primary object of the present invention to provide a flexible catheter with high flexibility, high specific freezing power and sufficiently small diameter for cryosurgical procedures in different areas of medicine.

It is another object of the invention to provide a rigid probe with high specific freezing power and sufficiently small diameter for cryosurgical procedures in different areas of medicine.

It is an additional object of the invention to design a cryosurgical instrument and its accessory system for cryosurgical procedures, which have high degree of safety and reliability. It should be noted that the proposed design of the cryosurgical instrument ensures positive temperatures at the distal section of its external shaft, especially, in the immediate vicinity of the cryotip.

It is another object of this invention to develop a novel method of thermal insulation of the distal section of the external shaft of the cryosurgical instrument, this method is based on the principle of a heat pipe.

It is another object of this invention to design a cryocatheter that is used for inhibiting restenosis of a blood vessel.

BRIEF DESCRIPTION OF THE SEVERAL VIEWS OF THE DRAWINGS

Other objectives of this invention will be apparent from the following detail description taken in conjunction with the accompanying drawings, in which.

Besides, this drawing demonstrates a general view of a cryosurgical instrument and a block diagram of its accessory system in the case of application of two different liquids for freezing and fast thawing a target tissue.

Figure 4:
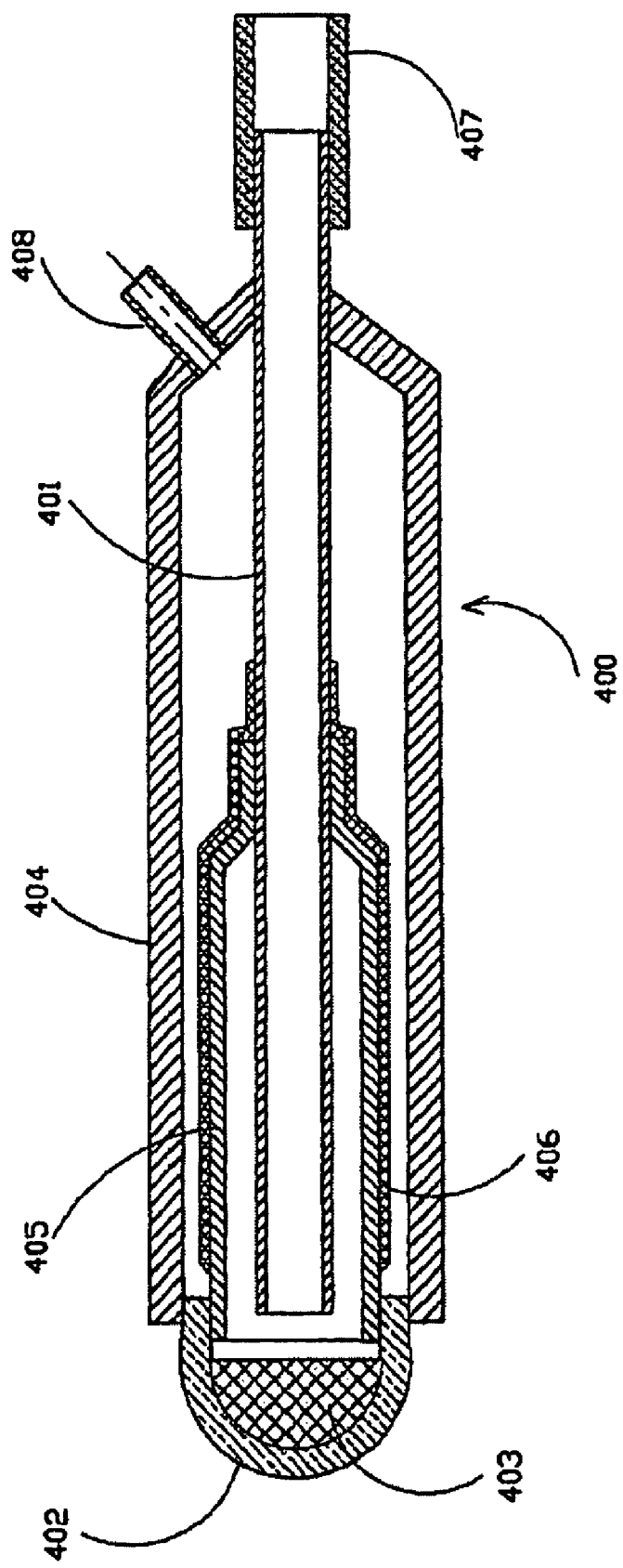

FIG. 4 is an axial cross-section of the cryosurgical instrument with application of active thermal insulation based of the principle of a heat pipe.

Figure 5:
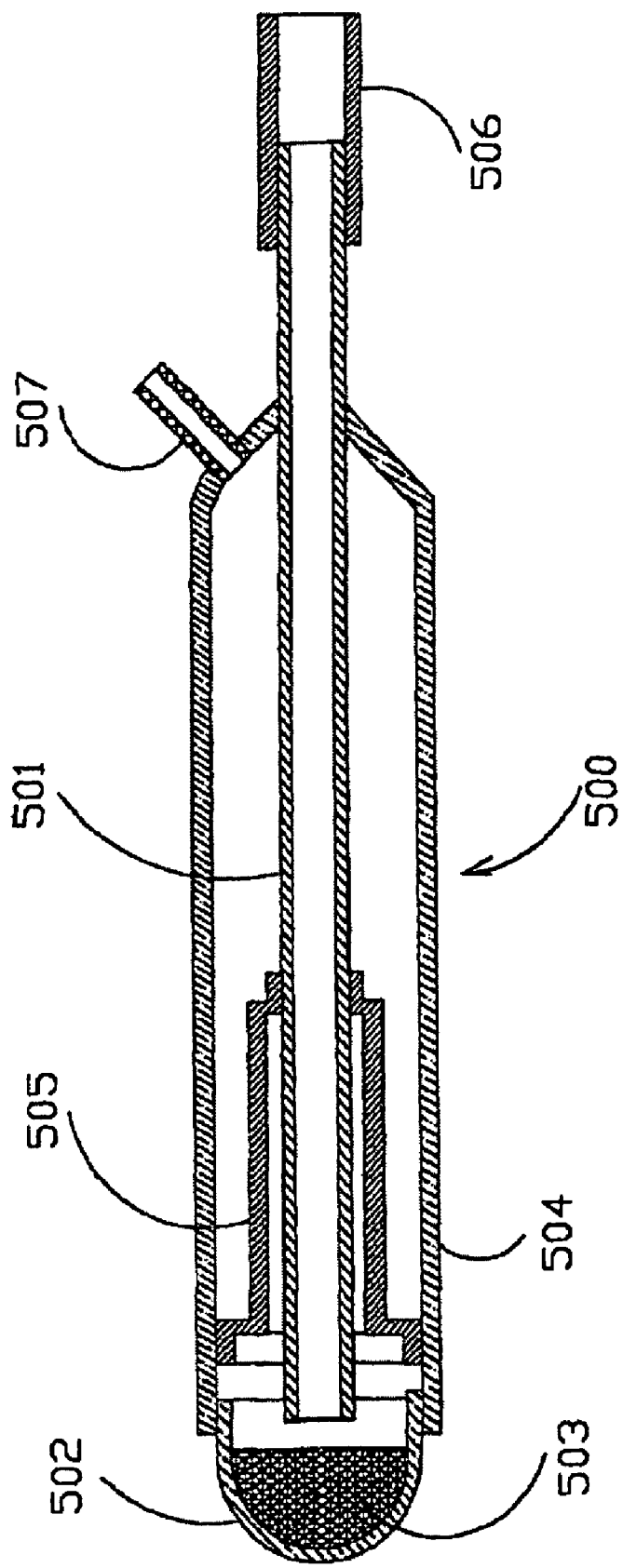

FIG. 5 is an axial cross-section of a cryosurgical instrument with a coaxial tubular piece joined at its distal end with the external shaft.

Figure 6:
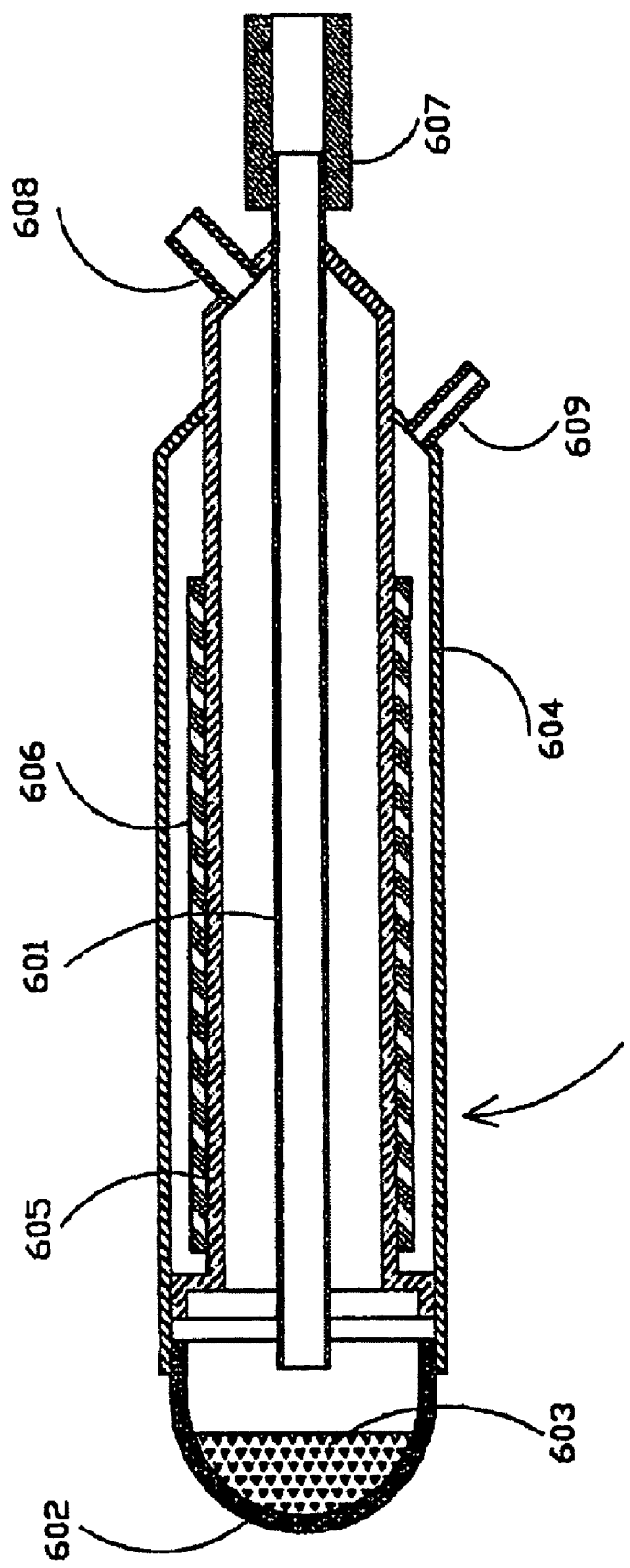

FIG. 6 demonstrates an axial cross-section of a cryosurgical instrument with application of the coaxial intermediate lumen instead of the coaxial tubular piece.

Figure 7:
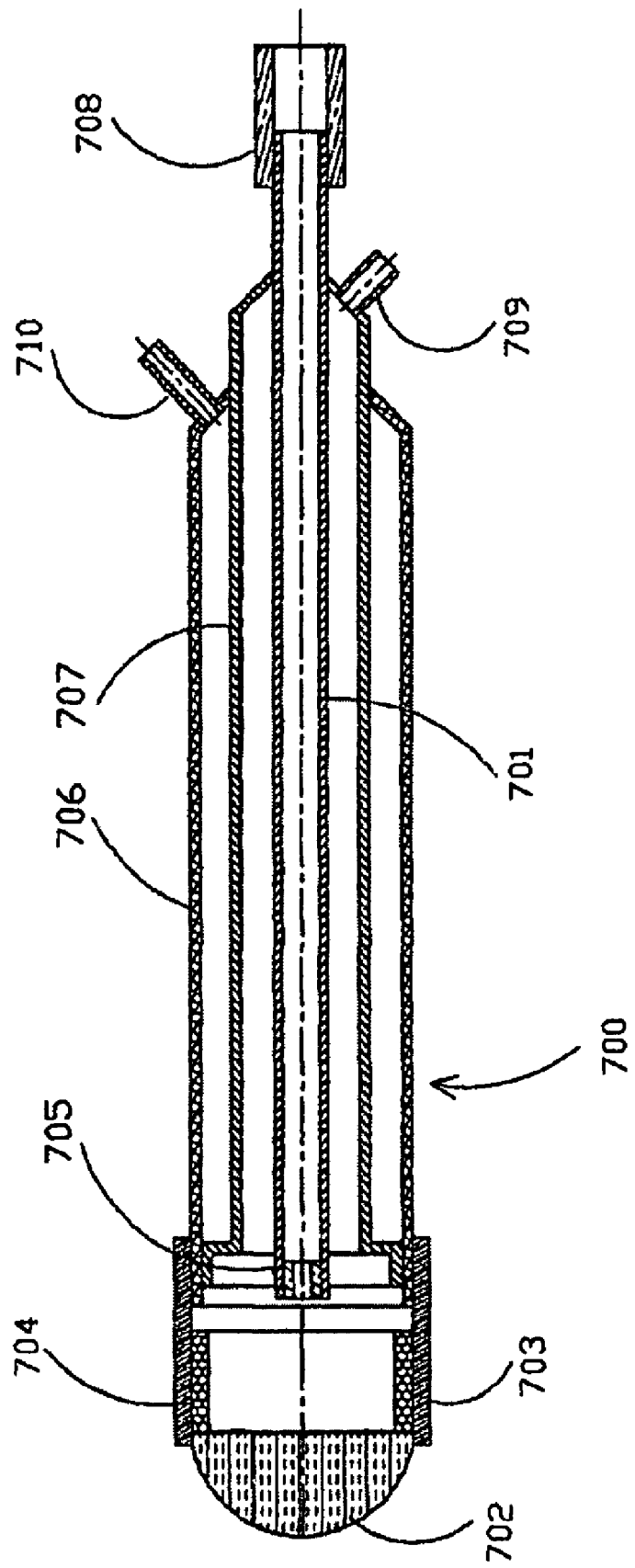

FIG. 7 is an axial cross-section of a cryocatheter for preventing restenosis of blood vessels.

DETAILED DESCRIPTION OF THE INVENTION

Figure 1:
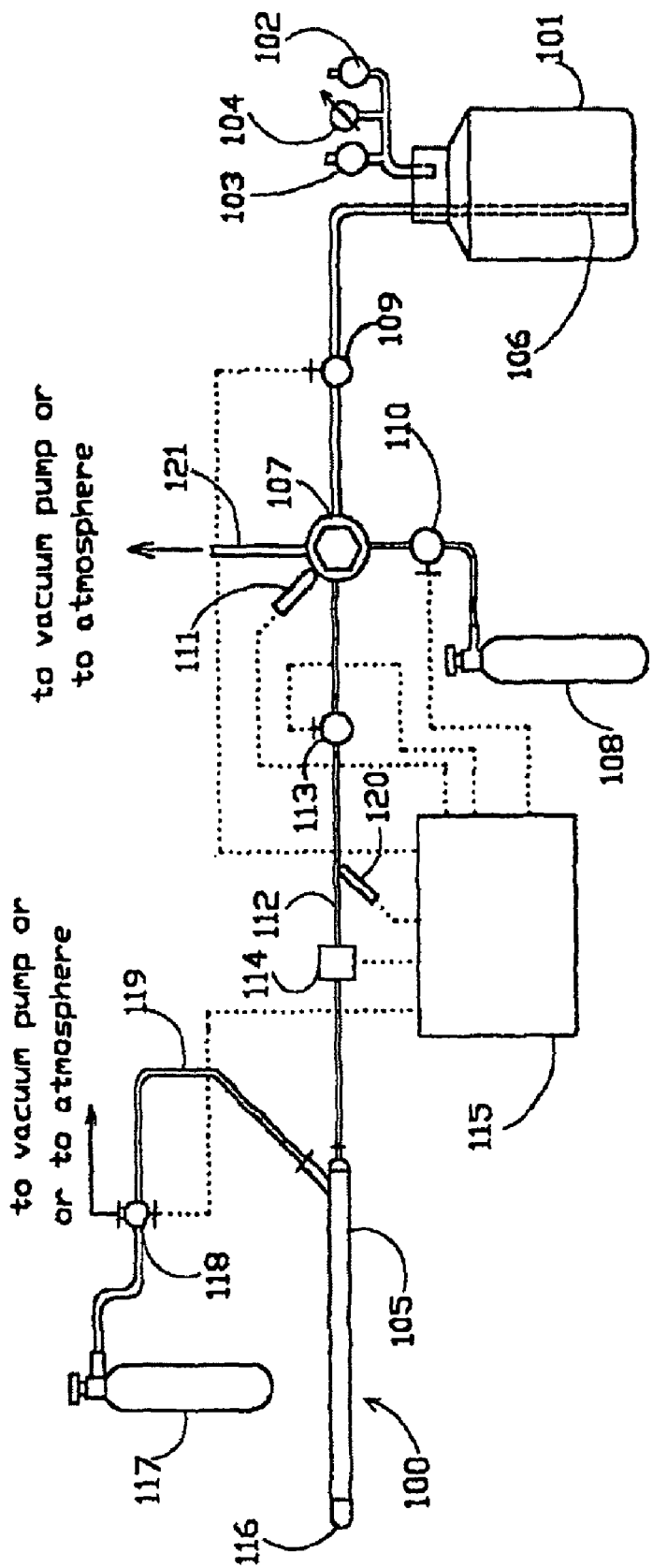
FIG. 1 is a general view of a cryosurgical instrument of the present invention and a block diagram of its accessory system.

FIG. 1 shows the general view of the cryosurgical instrument and its accessory device. The drawing demonstrates following units: a cryosurgical instrument 100 with cryotip 116 and an elongated tubular sub-unit 105. The accessory system comprises: a thermo-insulated tank (or a Dewar flask) 101 with cryogenic liquid, this thermo-insulated tank 101 is provided with a relief valve 103, which gives possibility to preset a desired pressure in the thermo-insulated tank, a shut-off valve 102 that serves for filling the thermo-insulated tank 101 with the cryogenic liquid, and manometer 104.

A multi-way valve 107 is communicated with: a feeding pipe 106 situated in the thermo-insulated tank 101; a vacuum pump or atmosphere (via duct 121); the cryosurgical instrument 100 by a main duct 112: bottle 108 with pressurized gas. Sensor 111 controls preset changeover frequency of the multi-way valve 107. In addition, there are pressure and temperature gauges 114 and 120 installed on the main duct 112. Data provided from these sensor and gauges are processed in a control unit 115. In the case of significant deviations of the measured parameters from the preset values, the control unit 115 cuts off the shut-off valves 109, 110 and 113.

In addition, there is bottle 117 filled with a gas with low thermal conductivity, for example, R14. This bottle is communicated via duct 119 with the external chamber of the cryosurgical instrument 100 (the gaps between the external shaft of the cryosurgical instrument 100, and its coaxial tubular piece, and the external shaft and the proximal section of the central feeding-venting lumen). A three-way valve 118 installed on duct 119 serves for filling the external chamber by charging and purging technique, this filling should be performed previously to actuating the cryosurgical instrument 100 and performance of cryogenic treatment.

Figure 2:
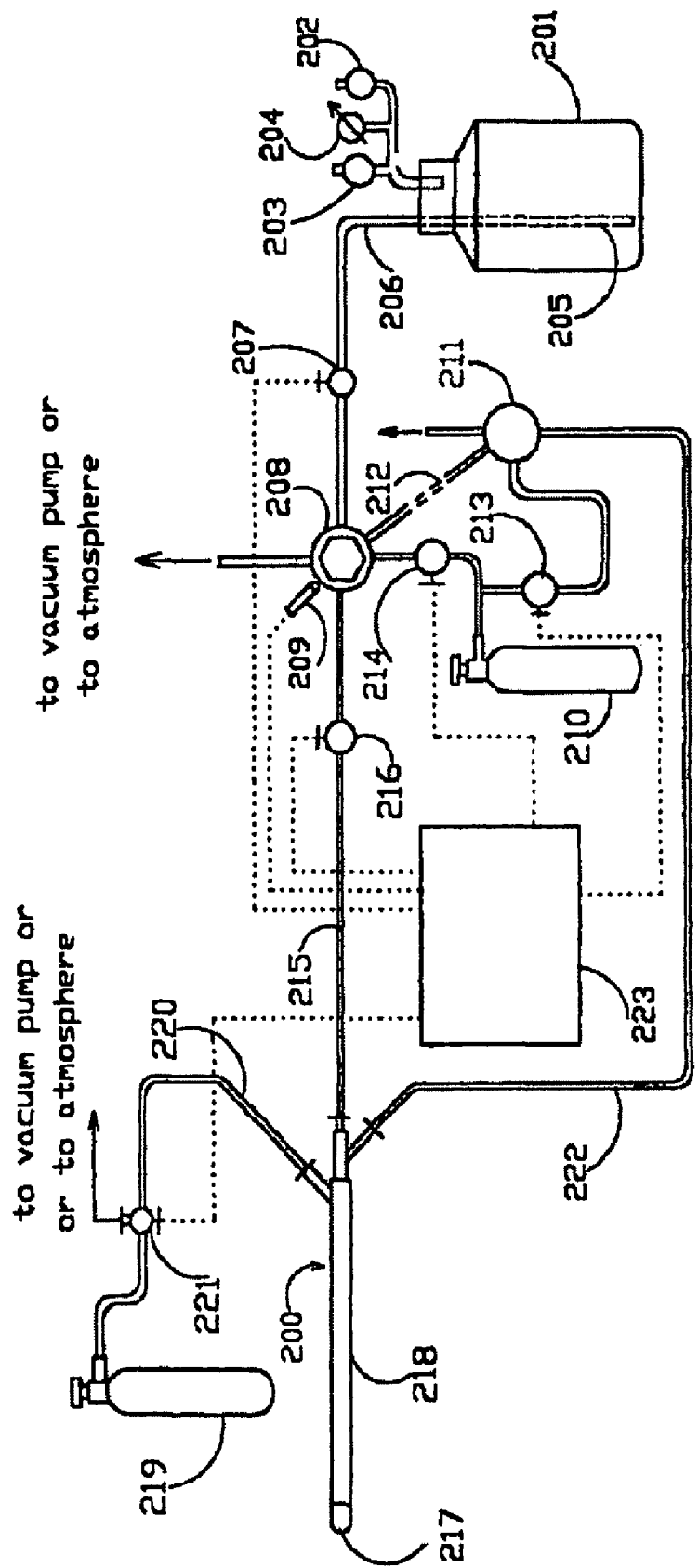
FIG. 2 is a general view of a cryosurgical instrument of the present invention and a block diagram of its accessory system, when there is a coaxial intermediate lumen situated between a central feeding-venting lumen and an external shaft with oscillating flow in the channel between the central feeding-venting and coaxial intermediate lumens.

FIG. 2 shows a cryosurgical instrument 200 and its accessory system in the case, when this cryosurgical instrument comprises a coaxial intermediate lumen instead of the coaxial tubular piece and there is oscillating flow in the channel between the central feeding-venting lumen and the coaxial intermediate lumen of the cryosurgical instrument. The cryosurgical instrument 200 consists of two major sub-units: 1) cryotip 217; 2) elongated tubular sub-unit 218.

The accessory system comprises a thermo-insulated tank (or a Dewar flask) 201 containing cryogenic liquid, this thermo-insulated tank 201 is provided with a relief valve 203 which gives possibility to preset a desired pressure in the thermo-insulated tank 201, valve 202 which serves for filling the thermo-insulated tank 201 with the cryogenic liquid, and manometer 204.

A multi-way valve 208 of the accessory system is communicated with following details: a feeding pipe 205 situated in the thermo-insulated tank 201; a vacuum pump or atmosphere; the cryosurgical instrument 200 (by a main duct 215); bottle 210 with pressurized gas. In addition, there is a three-way valve 211, which is joined mechanically by coupling 212 with the multi-way valve 208. The three-way valve is communicated with the channel between the coaxial intermediate lumen and the central feeding-venting lumen of the cryosurgical instrument 200 by duct 222, the atmosphere (or vacuum pump) and bottle 210 with pressurized gas. A shut-off valve 213 is installed on the duct, which communicates bottle 210 with the three-way valve 211. Coupling 212 is designed in such a way, that when the multi-way valve 208 communicates the main duct 215 with the atmosphere (or vacuum pump), then the three-way valve 211 communicates duct 222 with bottle 210 and vice versa, the three-way valve 211 communicates ducts 222 with the atmosphere (or vacuum pump) when the multi-way valve 208 communicates the main duct 215 with bottle 210.

Sensor 209 controls a preset changeover frequency of the multi-way valve 208. Data provided from this sensor are processed in a control unit 223. In the case of significant deviations of the measured parameters from the preset values, the control unit 223 cuts off a shut-off valve 207, which is installed on duct 206 communicating the feeding pipe 205 with the multi-way valve 208, a shut-off valve 214 installed on a duct communicating bottle 210 with the multi-way valve

208, a shut-off valve 216 installed on the main duct 215 and the shut-off valve 213 installed on a duct communicating bottle 210 with the three-way valve 211.

In addition, there is bottle 219 filled with a gas with low thermal conductivity, for example, R14. This bottle is communicated via duct 220 with the external chamber of the cryosurgical instrument 200 (the gap between the external shaft of the cryosurgical instrument 200 and its coaxial intermediate lumen). A three-way valve 221 installed on duct 220 serves for filling the external chamber of the cryosurgical instrument 200 with the gas with low thermal conductivity by charging and purging technique. This filling should be performed previously to actuating the cryosurgical instrument 200 and performance of cryogenic treatment.

Figure 3:
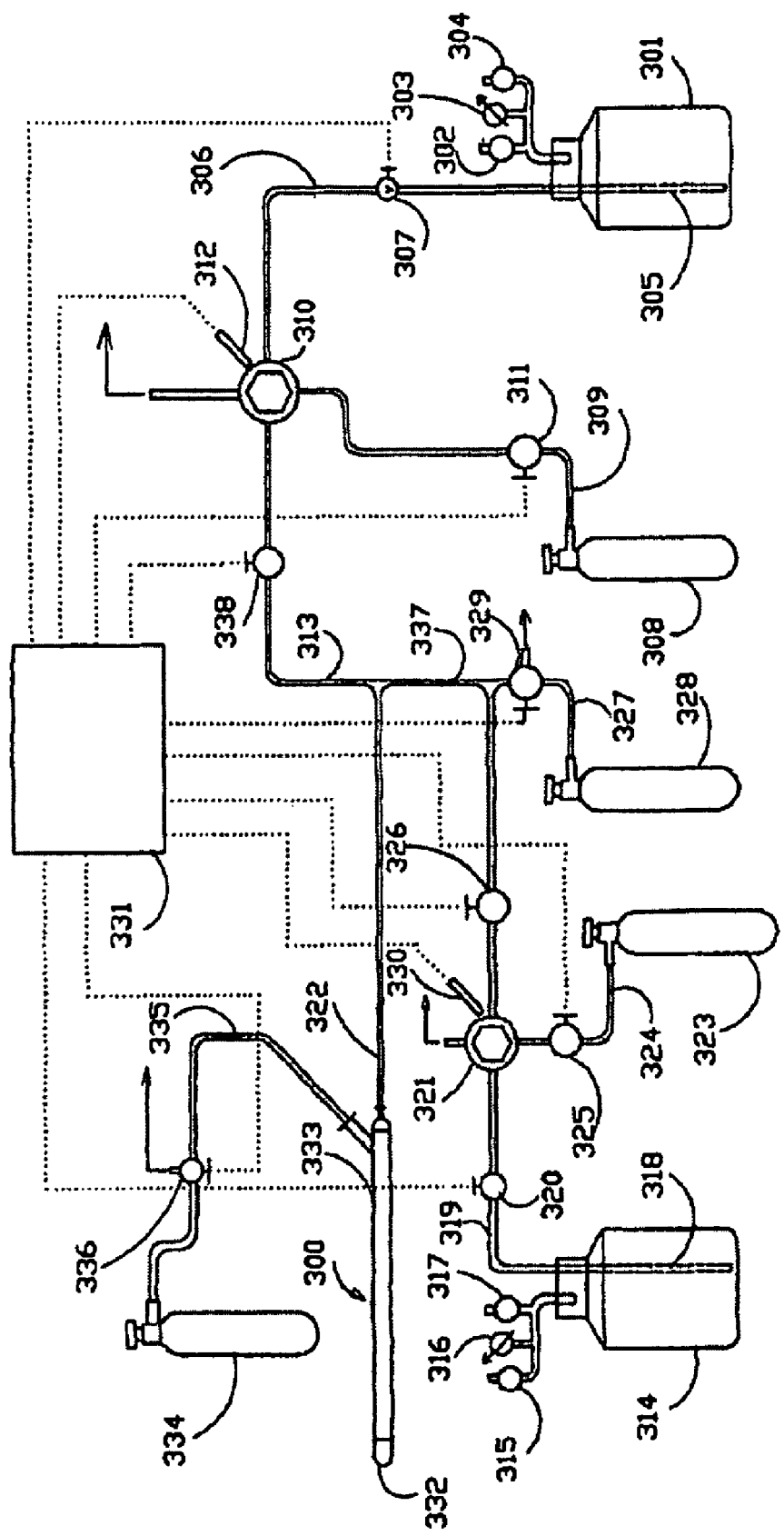
FIG. 3 is a general view of a cryosurgical instrument of the present invention and a block diagram of its accessory system, when two different liquids are used for preliminary ice-mapping and following cryogenic treatment.

FIG. 3 shows a general view of a cryosurgical instrument of the present invention and a block diagram of its accessory system, when two different liquids are used for preliminary ice-mapping and following cryogenic treatment.

In addition, this drawing demonstrates a general view of a cryosurgical instrument and a block diagram of its accessory system in the case of application of two different liquids for freezing and fast thawing a target tissue.

The drawing shows following units: a cryosurgical instrument 300 with cryotip 332 and an elongated tubular sub-unit 333. The accessory system comprises: a first tank 301 filled with first liquid with cryogenic boiling temperature (for example, liquid nitrogen), this first tank 301 is provided with: a relief valve 302, which gives possibility to preset the desired pressure in the first tank 301; valve 304 which serves for filling the first tank 301 with the first liquid and manometer 303.

A multi-way valve 310 is communicated by duct 306 with following details: a feeding pipe 305 situated in the first tank 301; a vacuum pump or the atmosphere; the cryosurgical instrument 300 by a main duct 322, this main duct splits off into two ducts 313 and 337; bottle 308 with a first pressurized gas. A shut-off valve 307 is installed on duct 306, a shut-off valve 338 is installed on duct 313 and a shut-off valve 309 is installed on a duct that communicates bottle 308 with the multi-way valve 310. Sensor 312 controls preset changeover frequency of the multi-way valve 310. Data provided from this sensor are processed in a control unit 331. In the case of significant deviation of the measured parameter from a preset value, the control unit 331 cuts off the shut-off valves 307,338 and 329.

In addition, the accessory system comprises a second tank 314 filled with second liquid with relatively high boiling temperature (for example, R12B 1), this second tank 314 is provided with: a relief valve 315 which gives possibility to preset the desired pressure in the second tank 314; valve 317 which serves for filling the second tank 314 with the second liquid; manometer 316.

A multi-way valve 321 is communicated with following details: by duct 319 with a feeding pipe 318 situated in the second tank 3141; a vacuum pump or the atmosphere; the cryosurgical instrument 300 by a main duct 322 and duct 337; bottle 323 with a second pressurized gas. A shut-off valve 320 is installed on duct 321, a shut-off valve 325 is installed on duct 324 communicating bottle 323 with the multi-way valve 321 and a shut-off valve 326 is installed on duct 337. Sensor 330 controls preset changeover frequency of the multi-way valve 321. Data provided from this sensor are processed in a control unit 331. In the case of significant deviation of the measured parameter from a preset value, the control unit 331 cuts off the shut-off valves 320, 325 and 326.

Bottle 328 with a third pressurized gas is communicated by duct 327 with ducts 337 and 322. A three-way valve 328 is installed on duct 327, this three-way valve is communicating with the atmosphere as well and the control unit 331 controls it. The three-way valve 329 serves for blowing the ducts and the cryosurgical instrument 300 itself after a stage of ice-mapping (or thawing) in order to remove the second liquid and its vapors. Charging and purging technique performs the blowing process.

In addition, there is bottle 334 filled with a gas with low thermal conductivity, for example, R14. This bottle is communicated by duct 335 with the external chamber of the cryosurgical instrument 300 (the gap between the external shaft of the cryosurgical instrument 300, and its coaxial tubular piece and the proximal section of the central feeding-venting lumen). A three-way valve 336 installed on duct 335 and communicated as well with the atmosphere serves for filling the external chamber of the cryosurgical instrument 300 by charging and purging technique, this filling should be performed previously to actuating the cryosurgical instrument 300 and performance of cryogenic treatment.

FIG. 4 shows an axial cross-section of a cryosurgical instrument 400 with application of active thermal insulation based of the principle of a heat pipe.

The cryosurgical instrument is constructed from two major sub-units: a distal cryotip 402, which serves for immediate contact with a target tissue; freezing action of this cryotip is obtained by evaporation of cryogenic liquid on its internal porous coating 403 formed from porous metal with open porosity; an elongated tubular sub-unit serving for delivery of portions of the cryogenic liquid on the internal porous coating 403 with following removal of vapors generated in the process of boiling this cryogenic liquid in the internal porous coating 403.

The elongated tubular sub-unit in turn comprises following details: an external shaft 404; a central feeding-venting lumen 401, which serves for immediate supply of portions of the cryogenic liquid to the internal porous coating 403 of the distal cryotip 402 and, at the same time, for removal of the vapors, generated in the process of boiling the cryogenic liquid in this internal coating 403, into the atmosphere or into a vacuum pump.

In addition, there is a coaxial tubular piece 405 positioned in the gap between the distal sections of the central feeding-venting lumen and the external shaft 404; the distal end of this coaxial tubular piece 405 is sealed with cryotip 402 and the proximal end-with the central feeding-venting lumen 401.

The outer surfaces of the coaxial tubular piece 405 and a section of the central feeding-venting lumen 401 mating this coaxial tubular piece are covered with a porous coating 406 with open porosity, this porous coating is functioning as a wick when the gap between the external shaft 404, the coaxial tubular piece 405 and the mating section of the central feeding-venting lumen 401 is filled with vapors of such a gas that its condensation temperature is higher than the boiling temperature of the applied cryogenic liquid.

The proximal end of the feeding-venting central lumen is provided with an inlet-outlet connection 407, and the proximal section of the external shaft 404 is provided with an inlet-outlet connection 408.

FIG. 5 is an axial cross-section of a cryosurgical instrument with a coaxial tubular piece joined at its distal end with the external shaft.

Cryocatheter 500 (or cryoprobe) is constructed from two major subunits: a distal cryotip 502, which serves for immediate contact with a target tissue, freezing action of this cryotip is obtained by evaporation of a cryogenic liquid in its internal porous coating 503 formed from porous metal with open porosity; an elongated tubular sub-unit serving for delivery of portions of the cryogenic liquid on the internal porous coating 503 with following removal of vapors generated in the process of boiling this cryogenic liquid in the internal porous coating 503.

The elongated tubular sub-unit in turn comprises following details: an external shaft 504 and a central feeding-venting lumen 501, which serves for immediate supply of portions of the cryogenic liquid to the internal porous coating 503 of the distal cryotip 502 and, at the same time, for removal of the vapors generated in the process of boiling the cryogenic liquid on this internal porous coating 503 into the atmosphere or into a vacuum pump.

In addition, there is a coaxial tubular piece 505 positioned in the gap between the distal sections of the central feeding-venting lumen 501 and the external shaft 504; the distal end of this coaxial tubular piece 505 is sealed with the external shaft 504 and its proximal end—with the central feeding-venting lumen 501. The proximal end of the feeding-venting central lumen 501 is provided with an inlet-outlet connection 506, and the proximal section of the external shaft 504 is provided with an inlet-outlet connection 507.

FIG. 6 demonstrates an axial cross-section of the cryosurgical instrument with application of a coaxial intermediate lumen instead of the coaxial tubular piece.

A cryosurgical instrument 600 is constructed from two major sub-units: a distal cryotip 602, which serves for immediate contact with a target tissue; freezing action of this cryotip is obtained by evaporation of a cryogenic liquid on its internal porous coating 603 formed from porous metal with open porosity; an elongated tubular sub-unit serving for delivery of portions of the cryogenic liquid on the porous coating with following removal of vapors generated in the process of boiling this cryogenic liquid in the internal porous coating 603.

The elongated tubular sub-unit in turn comprises following details: an external shaft 604 and a central feeding-venting lumen 601, which serves for immediate supply of portions of the cryogenic liquid to the internal porous coating 603 of the distal cryotip 602 and, at the same time, for removal of the vapors, generated in the process of boiling the cryogenic liquid in this internal coating 603, into the atmosphere or into a vacuum pump.

In addition, there is a coaxial intermediate lumen 605 positioned in the gap between the central feeding-venting lumen 601 and the external shaft 604; the distal end of this coaxial intermediate lumen 605 is sealed with the external shaft 604 and the proximal end—with the central feeding-venting lumen 601. In addition, the proximal end of the external shaft 604 is sealed with the proximal section of the coaxial intermediate lumen 605. The proximal end of the feeding-venting central lumen 601 is provided with an inlet-outlet connection 607, the proximal section of the external shaft 604 is provided with an inlet-outlet connection 609 and proximal section of the coaxial intermediate lumen 605 is provided with an inlet-outlet connection 608. Significant part of the outer surface of the coaxial intermediate lumen 605 is covered with a porous coating 606 leading off with the proximal end of the intermediate lumen, this porous coating serves as a wick in the case of application of the principle of a heat pipe for heating the distal section of the external shaft.

FIG. 7 demonstrates an axial cross-section of the catheter for preventing restenosis of blood vessels.

Cryocatheter 700 is constructed from two major sub-units: a distal cryotip, which serves for immediate contact with a target tissue; freezing action of this cryotip is obtained by evaporation of a cryogenic liquid in an internal porous coating 704 formed from porous elastic polymer with open porosity on the internal surface of an external tubular piece 703, which is made from elastic polymer as well.

The distal end of external tubular piece 703 is sealed by plug 702 manufactured from polymer material with low thermal conductivity.

What is claimed is:

1. A method for cryogenic treatment of a patient, comprising:
    contacting a portion of the patient with a cryosurgical instrument, said instrument having a tip;
    delivering a cryogen to said tip; and
    repeating said delivering said cryogen to said tip at least once while said tip is in contact with at least a portion of the patient, wherein controlling said delivering of said cryogen to said tip also controls temperature at said tip, such that the delivering and the repeating said delivering produce at least one freezing stage and at least one higher temperature freezing stage, and wherein said instrument comprises a plurality of valves for controlling said delivering said cryogen and wherein said repeating said delivering said cryogen to said tip at least once comprises: closing a valve to stop delivering said cryogen, and opening a valve to again deliver said cryogen, by opening a first valve of said plurality of valves to expel said cryogen to the atmosphere, closing said first valve, and opening a second valve of said plurality of valves to deliver said cryogen.

2. The method of claim 1, wherein said portion of the patient comprises a blood vessel.

3. The method of claim 2, wherein the cryogenic treatment is for prevention of restenosis.

4. The method of claim 1, wherein said instrument further comprises a control unit and wherein said control unit controls said opening and said closing of said valves to control temperature at said tip.

5. The method of claim 4, further comprising determining said temperature at said tip by said control unit; and controlling said opening and said closing of said valves by said control unit according to said temperature.

6. The method of claim 1, wherein said delivering said cryogen to said tip comprises:
    pressurizing said cryogen for rapid delivery to said tip.

7. The method of claim 6, wherein said pressurizing comprises applying gas to said cryogen.

8. The method of claim 1, wherein said cryogen comprises a plurality of cryogens having different properties.

9. The method of claim 1, wherein said cryogen comprises at least one cryogenic liquid.

10. The method of claim 9, wherein said cryogen comprises a plurality of cryogenic liquids.

11. The method of claim 1, further comprising ablating tissue of said portion of the patient through said at least one freezing stage and said at least one higher temperature freezing stage.

12. The method of claim 1, wherein said cryogen is delivered in a plurality of portions and wherein said temperature is controlled at said tip according to a frequency of repeating said delivering of said portions of said cryogen to said tip.

* * * * *